US012577538B2

(12) United States Patent
Clark et al.

(10) Patent No.: US 12,577,538 B2
(45) Date of Patent: Mar. 17, 2026

(54) SYSTEMS AND METHODS FOR GENERATING BACTERIOPHAGES ADAPTED TO INFECT A TARGET BACTERIAL STRAIN

(71) Applicant: Baylor College of Medicine, Houston, TX (US)

(72) Inventors: Justin Clark, Houston, TX (US); Sabrina Green, Houston, TX (US); Keiko Salazar, Houston, TX (US); Austen Terwilliger, Houston, TX (US); Anthony Maresso, Missouri City, TX (US)

(73) Assignee: Baylor College of Medicine, Houston, TX (US)

( * ) Notice: Subject to any disclaimer, the term of this patent is extended or adjusted under 35 U.S.C. 154(b) by 1051 days.

(21) Appl. No.: 17/596,589

(22) PCT Filed: Jun. 25, 2020

(86) PCT No.: PCT/US2020/039527
§ 371 (c)(1),
(2) Date: Dec. 14, 2021

(87) PCT Pub. No.: WO2020/264096
PCT Pub. Date: Dec. 30, 2020

(65) Prior Publication Data
US 2022/0340882 A1    Oct. 27, 2022

Related U.S. Application Data

(60) Provisional application No. 62/867,388, filed on Jun. 27, 2019.

(51) Int. Cl.
*C12N 7/00* (2006.01)
*C12M 1/00* (2006.01)
*C12N 1/20* (2006.01)

(52) U.S. Cl.
CPC .............. *C12N 7/00* (2013.01); *C12M 23/40* (2013.01); *C12M 23/58* (2013.01); *C12M 29/04* (2013.01); *C12N 1/20* (2013.01); *C12N 2795/10121* (2013.01); *C12N 2795/10131* (2013.01); *C12N 2795/10151* (2013.01)

(58) Field of Classification Search
None
See application file for complete search history.

(56) References Cited

U.S. PATENT DOCUMENTS

| | | | |
|---|---|---|---|
| 7,758,856 B2 | 7/2010 | Hughes | |
| 2012/0040329 A1* | 2/2012 | Baldwin | C12N 7/00 435/235.1 |

FOREIGN PATENT DOCUMENTS

| | | | |
|---|---|---|---|
| SI | 24571 A | 6/2015 | |
| WO | 95/23848 A1 | 9/1995 | |
| WO | 2010/064044 A1 | 6/2010 | |
| WO | 2014/001504 A2 | 1/2014 | |
| WO | 2015/134121 A9 | 9/2015 | |
| WO | WO-2015134121 A2 * | 9/2015 | C40B 50/06 |

OTHER PUBLICATIONS

Salazar, et al. mBio. Apr. 27, 2021;12(2):e00211-21. doi: 10.1128/mBio.00211-21. PMID: 33906920. (Year: 2021).*
"Communication Pursuant to Rules 70(2) and 70a(2) EPC, European Patent Application No. 20831131.6", Jul. 14, 2023, 1 page.
"Communication, Extended European Search Report, European Patent Application No. 20831131.6", Jun. 27, 2023, 12 pages.
Betts, A., et al., "Back to the future: evolving bacteriophages to increase their effectiveness against the pathogen Pseudomonas aeruginosa PAO1", Evolutionary Applications 6, 2013, 1054-1063.
Esvelt, K. M., et al., "A system for the continuous directed evolution of biomolecules", Nature, vol. 472, Apr. 28, 2011, 499-506.
Green, S. I., et al., "Bacteriophages from ExPEC Reservoirs Kill Pandemic Multidrug-Resistant Strains of Clonal Group ST131 in Animal Models of Bacteremia", Scientific Reports, Apr. 12, 2017, 13 pages.
Salazar, K. C., et al., "Antiviral Resistance and Phage Counter Adaptation to Antibiotic-Resistant Extraintestinal Pathogenic *Escherichia coli*", mBio, Apr. 27, 2021, 20 pages.
Wikipedia, "Chemostat", https://en.wikipedia.org/wiki/Chemostat, downloaded Apr. 30, 2019, 8 pages.
Green, Sabrina I. et al., "Bacteriophages from ExPEC Reservoirs Kill Pandemic Multidrug-Resistant Strains of Clonal Group ST131 in Animal Models of Bacteremia", Scientific Reports 7:46151, Apr. 12, 2017, 13 pages.
Ma, L., et al., "Metals Enhance the Killing of Bacteria by Bacteriophage in Human Blood", Scientific Reports 8:2326, Feb. 2, 2018, 11 pages.
Miller, A. W., et al., "Design and Use of Multiplexed Chemostat Arrays", Journal of Visualized Experiments 72, Feb. 2013, 6 pages.
Pathak, D., "Bacteriophages, natural drugs to combat superbugs", Apr. 18, 2017, 4 pages.

(Continued)

*Primary Examiner* — Benjamin P Blumel
*Assistant Examiner* — Jeffrey Mark Sifford
(74) *Attorney, Agent, or Firm* — Saul Ewing LLP; Kathryn Doyle; Justin W. Crotty

(57) ABSTRACT

One aspect of the invention provides a method of generating bacteriophages adapted to infect a target bacterial strain. The method comprises: providing host bacteria that are susceptible to phage as input to a host chemostat containing phage; providing target bacteria that are related to the host bacteria, but not susceptible to phage as input to a target chemostat containing phage; filtering outflows from the host chemostat and the target chemostat to isolate phage from the populations of the host bacteria, the target bacteria, and macromolecules; combining the outflows; and introducing the combined outflow into each of the host chemostat and the target chemostat.

4 Claims, 12 Drawing Sheets

Specification includes a Sequence Listing.

(56)             References Cited

OTHER PUBLICATIONS

Wichman, H. A., et al., "Adaptive Molecular Evolution for 13,000 Phage Generations: A Possible Arms Race", Genetics 170: 19-31, May 2005.

International Search Report and Written Opinion, International Patent Application No. PCT/US2020/039527, Sep. 24, 2020.

\* cited by examiner

Figure 1:
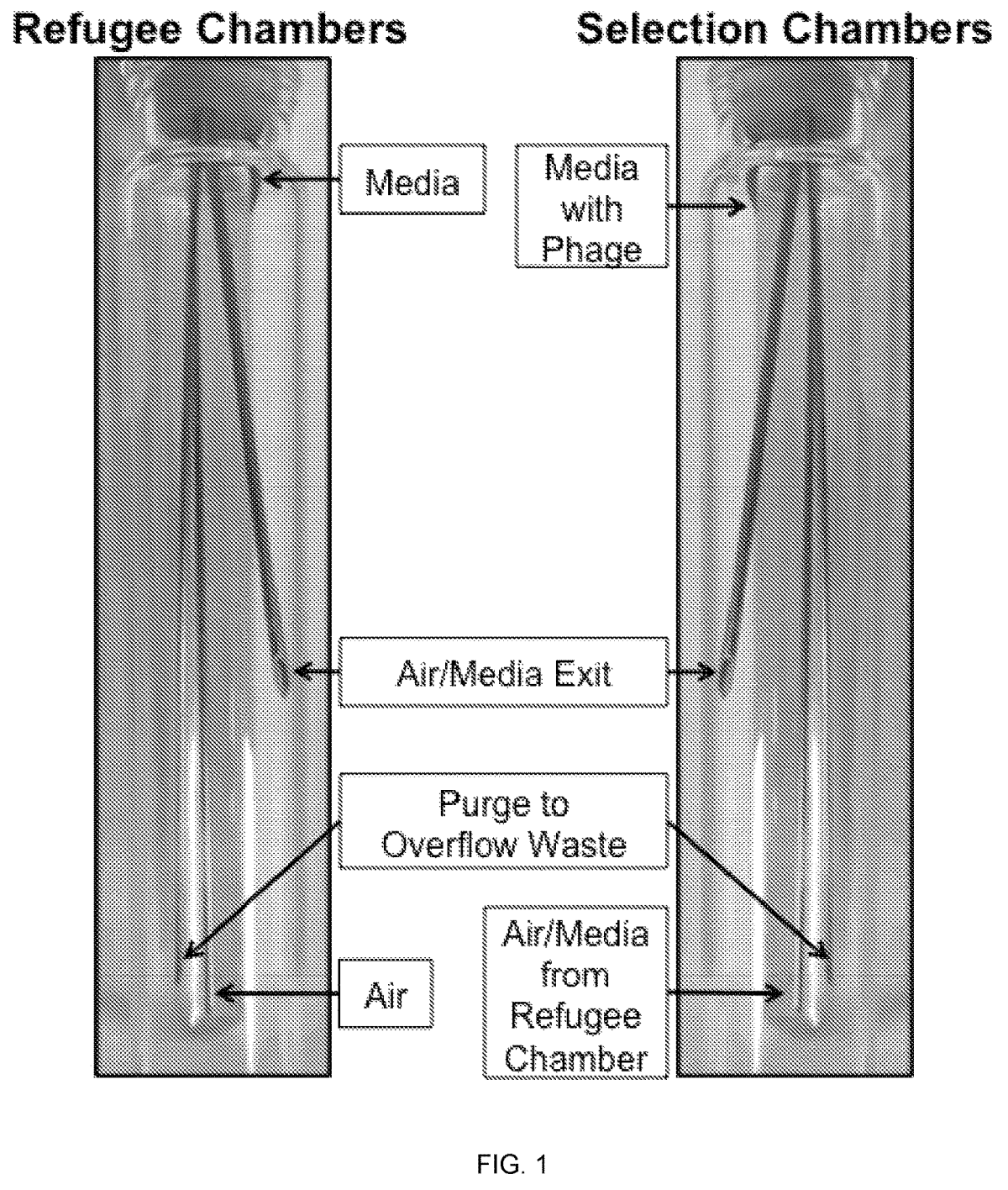

Refugee Chambers                    Selection Chambers

Media

Media with Phage

Air/Media Exit

Purge to Overflow Waste

Air

Air/Media from Refugee Chamber

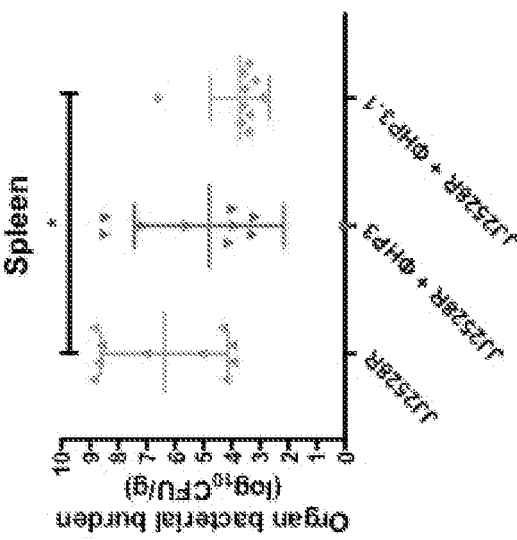
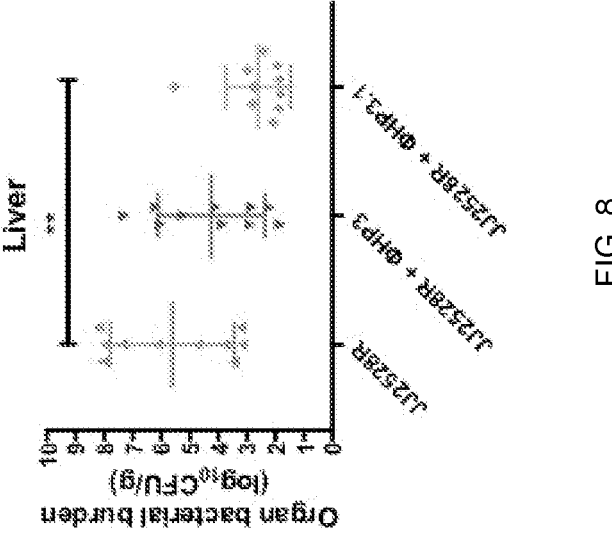
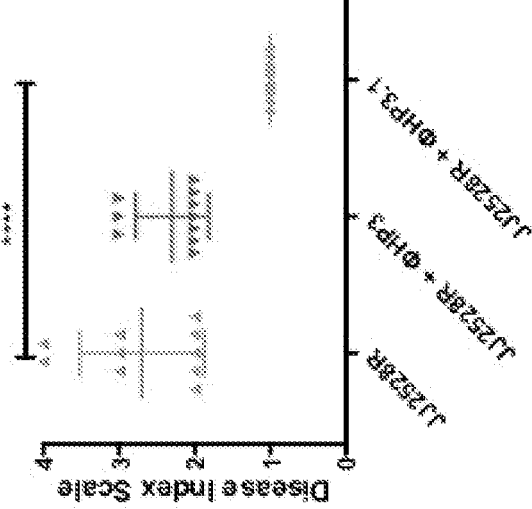
FIG. 8

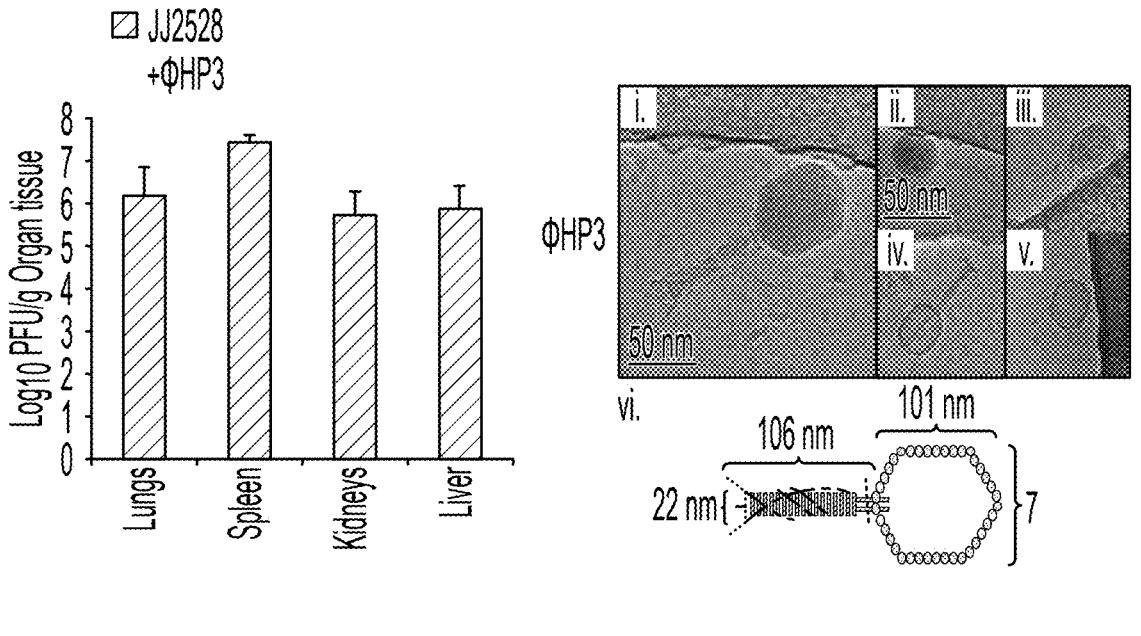
FIG. 9D                    FIG. 9E

| | | | |
|---|---|---|---|
| HP3_Short_Tail_Fiber/1-516 | 1 | MSNNTYQHVSNESKYVKFDPTGSNFPGTVTTVQSALSKISNIGVNGIPDATMEVKGIAMI | 60 |
| HP3.1_Short_Tail_Fiber/1-516 | 1 | MSNNTYQHVSNESKYVKFDPTGSNFPGTVTTVQSALSKISNIGVNGIPDATMEVKGIAMI | 60 |
| HP3_Short_Tail_Fiber/1-516 | 61 | ASEQEVLDGTNNSKIVTPATLATRLLYPNATETKYGLTRYSTNEETLKGSDNNSSITPQK | 120 |
| HP3.1_Short_Tail_Fiber/1-516 | 61 | ASEQEVLDGTNNSKIVTPATLATRLLYPNATETKYGLTRYSTNEETLKGSDNNSSITPQK | 120 |
| HP3_Short_Tail_Fiber/1-516 | 121 | LKYHTDDVFKNRYSSESSNGVIKISSTPAALAGVDDTTAMTPLKTQKLAIKLISQIAPSE | 180 |
| HP3.1_Short_Tail_Fiber1/-516 | 121 | LKYHTDDVFKNRYSSESSNGVIKISSTPAALAGVDDTTAMTPLKTQKLAIKLISQIAPSE | 180 |
| HP3_Short_Tail_Fiber/1-516 | 181 | DTATESVRGVVQLSTVAQIRQGTLREGYAISPYTFMNSVATHEYKGVIRLGTQTEINNNL | 240 |
| HP3.1_Short_Tail_Fiber/1-516 | 181 | DTATESVRGVVQLSTVAQIRQGTLREGYAISPYTFMNSVATHEYKGVIRLGTQTEINNNL | 240 |
| HP3_Short_Tail_Fiber/1-516 | 241 | GGVAVTGETLNGRGATGSMRGVVKLTTQAGIAPEGDSSGALAWNADVINTRGGQTINGSL | 300 |
| HP3.1_Short_Tail_Fiber/1-516 | 241 | GGVAVTGETLNGRGATGSMRGVVKLTTQAGIAPEGDSSGALAWNADVINTRGGQTINGSL | 300 |
| HP3_Short_Tail_Fiber/1-516 | 301 | NLDHLTANGIWSRGGMWKNGDQPVATERYASERVPVGTIMMFAGDSAPPGWIMCHGGTVS | 360 |
| HP3.1_Short_Tail_Fiber/1-516 | 301 | NLDHLTANGIWSRGGMWKNGDQPVATERYASERVPVGTIMMFAGDSAPPGWIMCHGGTVS | 360 |
| HP3_Short_Tail_Fiber/1-516 | 361 | GDQFPDYRNVVGTRFGGDWNNPGVPDMRGLFVRGAGTGGHILNQRGQDGYGKDRLGVGCD | 420 |
| HP3.1_Short_Tail_Fiber/1-516 | 361 | GDQFPDYRNVVGTRFGGDWNNPGVPDMRGLFVRGAGTGGHILNQRGQDGYGKDRLGVGCD | 420 |
| HP3_Short_Tail_Fiber/1-516 | 421 | GMHVGGVQAQQMSYHKHAGGWGEYNRSEGPFGASVYQGYLGTRKYSDWDNASYFTNDGFE | 480 |
| HP3.1_Short_Tail_Fiber/1-516 | 421 | GMHVGGVQAQQMSYHKHAGGWGEYNRSEGPFGASVYQGYLGTRRHSDWDNASYFTNDGFE | 480 |
| HP3_Short_Tail_Fiber/1-516 | 481 | LGGPRDAHGTLNREGLIGYETRPWNISLNYIIKVHY (SEQ ID NO: 1) | 516 |
| HP3.1_Short_Tail_Fiber/1-516 | 481 | LGGPRDAHGTLNREGLIGYETRPWNISLNYIIKVHY (SEQ ID NO: 2) | 516 |

FIG. 11

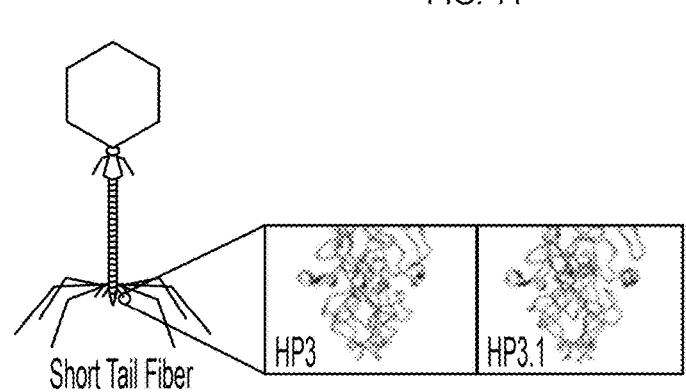

FIG. 12

SEQUENCE LISTING

```
<160> NUMBER OF SEQ ID NOS: 2

<210> SEQ ID NO 1
<211> LENGTH: 516
<212> TYPE: PRT
<213> ORGANISM: Bacteriophage HP3

<400> SEQUENCE: 1

Met Ser Asn Asn Thr Tyr Gln His Val Ser Asn Glu Ser Lys Tyr Val
1               5                   10                  15

Lys Phe Asp Pro Thr Gly Ser Asn Phe Pro Gly Thr Val Thr Thr Val
            20                  25                  30

Gln Ser Ala Leu Ser Lys Ile Ser Asn Ile Gly Val Asn Gly Ile Pro
        35                  40                  45

Asp Ala Thr Met Glu Val Lys Gly Ile Ala Met Ile Ala Ser Glu Gln
    50                  55                  60

Glu Val Leu Asp Gly Thr Asn Asn Ser Lys Ile Val Thr Pro Ala Thr
65                  70                  75                  80

Leu Ala Thr Arg Leu Leu Tyr Pro Asn Ala Thr Glu Thr Lys Tyr Gly
            85                  90                  95

Leu Thr Arg Tyr Ser Thr Asn Glu Glu Thr Leu Lys Gly Ser Asp Asn
            100                 105                 110

Asn Ser Ser Ile Thr Pro Gln Lys Leu Lys Tyr His Thr Asp Asp Val
        115                 120                 125

Phe Lys Asn Arg Tyr Ser Ser Glu Ser Ser Asn Gly Val Ile Lys Ile
    130                 135                 140

Ser Ser Thr Pro Ala Ala Leu Ala Gly Val Asp Asp Thr Thr Ala Met
145                 150                 155                 160

Thr Pro Leu Lys Thr Gln Lys Leu Ala Ile Lys Leu Ile Ser Gln Ile
                165                 170                 175

Ala Pro Ser Glu Asp Thr Ala Thr Glu Ser Val Arg Gly Val Val Gln
            180                 185                 190

Leu Ser Thr Val Ala Gln Ile Arg Gln Gly Thr Leu Arg Glu Gly Tyr
        195                 200                 205

Ala Ile Ser Pro Tyr Thr Phe Met Asn Ser Val Ala Thr His Glu Tyr
```

-continued

```
            210             215             220

Lys Gly Val Ile Arg Leu Gly Thr Gln Thr Glu Ile Asn Asn Asn Leu
225             230             235             240

Gly Gly Val Ala Val Thr Gly Glu Thr Leu Asn Gly Arg Gly Ala Thr
                245             250             255

Gly Ser Met Arg Gly Val Val Lys Leu Thr Thr Gln Ala Gly Ile Ala
            260             265             270

Pro Glu Gly Asp Ser Ser Gly Ala Leu Ala Trp Asn Ala Asp Val Ile
            275             280             285

Asn Thr Arg Gly Gly Gln Thr Ile Asn Gly Ser Leu Asn Leu Asp His
            290             295             300

Leu Thr Ala Asn Gly Ile Trp Ser Arg Gly Gly Met Trp Lys Asn Gly
305             310             315             320

Asp Gln Pro Val Ala Thr Glu Arg Tyr Ala Ser Glu Arg Val Pro Val
                325             330             335

Gly Thr Ile Met Met Phe Ala Gly Asp Ser Ala Pro Pro Gly Trp Ile
            340             345             350

Met Cys His Gly Gly Thr Val Ser Gly Asp Gln Phe Pro Asp Tyr Arg
            355             360             365

Asn Val Val Gly Thr Arg Phe Gly Gly Asp Trp Asn Asn Pro Gly Val
            370             375             380

Pro Asp Met Arg Gly Leu Phe Val Arg Gly Ala Gly Thr Gly Gly His
385             390             395             400

Ile Leu Asn Gln Arg Gly Gln Asp Gly Tyr Gly Lys Asp Arg Leu Gly
                405             410             415

Val Gly Cys Asp Gly Met His Val Gly Gly Val Gln Ala Gln Gln Met
                420             425             430

Ser Tyr His Lys His Ala Gly Gly Trp Gly Glu Tyr Asn Arg Ser Glu
            435             440             445

Gly Pro Phe Gly Ala Ser Val Tyr Gln Gly Tyr Leu Gly Thr Arg Lys
            450             455             460

Tyr Ser Asp Trp Asp Asn Ala Ser Tyr Phe Thr Asn Asp Gly Phe Glu
465             470             475             480

Leu Gly Gly Pro Arg Asp Ala His Gly Thr Leu Asn Arg Glu Gly Leu
                485             490             495

Ile Gly Tyr Glu Thr Arg Pro Trp Asn Ile Ser Leu Asn Tyr Ile Ile
            500             505             510

Lys Val His Tyr
            515

<210> SEQ ID NO 2
<211> LENGTH: 516
<212> TYPE: PRT
<213> ORGANISM: Bacteriophage HP3.1

<400> SEQUENCE: 2

Met Ser Asn Asn Thr Tyr Gln His Val Ser Asn Glu Ser Lys Tyr Val
1               5               10              15

Lys Phe Asp Pro Thr Gly Ser Asn Phe Pro Gly Thr Val Thr Thr Val
                20              25              30

Gln Ser Ala Leu Ser Lys Ile Ser Asn Ile Gly Val Asn Gly Ile Pro
            35              40              45

Asp Ala Thr Met Glu Val Lys Gly Ile Ala Met Ile Ala Ser Glu Gln
    50              55              60
```

```
Glu Val Leu Asp Gly Thr Asn Asn Ser Lys Ile Val Thr Pro Ala Thr
65              70              75              80

Leu Ala Thr Arg Leu Leu Tyr Pro Asn Ala Thr Glu Thr Lys Tyr Gly
            85              90              95

Leu Thr Arg Tyr Ser Thr Asn Glu Glu Thr Leu Lys Gly Ser Asp Asn
            100             105             110

Asn Ser Ser Ile Thr Pro Gln Lys Leu Lys Tyr His Thr Asp Asp Val
        115             120             125

Phe Lys Asn Arg Tyr Ser Ser Glu Ser Ser Asn Gly Val Ile Lys Ile
    130             135             140

Ser Ser Thr Pro Ala Ala Leu Ala Gly Val Asp Asp Thr Thr Ala Met
145             150             155             160

Thr Pro Leu Lys Thr Gln Lys Leu Ala Ile Lys Leu Ile Ser Gln Ile
            165             170             175

Ala Pro Ser Glu Asp Thr Ala Thr Glu Ser Val Arg Gly Val Val Gln
            180             185             190

Leu Ser Thr Val Ala Gln Ile Arg Gln Gly Thr Leu Arg Glu Gly Tyr
        195             200             205

Ala Ile Ser Pro Tyr Thr Phe Met Asn Ser Val Ala Thr His Glu Tyr
    210             215             220

Lys Gly Val Ile Arg Leu Gly Thr Gln Thr Glu Ile Asn Asn Asn Leu
225             230             235             240

Gly Gly Val Ala Val Thr Gly Glu Thr Leu Asn Gly Arg Gly Ala Thr
            245             250             255

Gly Ser Met Arg Gly Val Val Lys Leu Thr Thr Gln Ala Gly Ile Ala
            260             265             270

Pro Glu Gly Asp Ser Ser Gly Ala Leu Ala Trp Asn Ala Asp Val Ile
            275             280             285

Asn Thr Arg Gly Gly Gln Thr Ile Asn Gly Ser Leu Asn Leu Asp His
    290             295             300

Leu Thr Ala Asn Gly Ile Trp Ser Arg Gly Gly Met Trp Lys Asn Gly
305             310             315             320

Asp Gln Pro Val Ala Thr Glu Arg Tyr Ala Ser Glu Arg Val Pro Val
            325             330             335

Gly Thr Ile Met Met Phe Ala Gly Asp Ser Ala Pro Pro Gly Trp Ile
            340             345             350

Met Cys His Gly Gly Thr Val Ser Gly Asp Gln Phe Pro Asp Tyr Arg
        355             360             365

Asn Val Val Gly Thr Arg Phe Gly Gly Asp Trp Asn Asn Pro Gly Val
    370             375             380

Pro Asp Met Arg Gly Leu Phe Val Arg Gly Ala Gly Thr Gly Gly His
385             390             395             400

Ile Leu Asn Gln Arg Gly Gln Asp Gly Tyr Gly Lys Asp Arg Leu Gly
            405             410             415

Val Gly Cys Asp Gly Met His Val Gly Gly Val Gln Ala Gln Gln Met
            420             425             430

Ser Tyr His Lys His Ala Gly Gly Trp Gly Glu Tyr Asn Arg Ser Glu
        435             440             445

Gly Pro Phe Gly Ala Ser Val Tyr Gln Gly Tyr Leu Gly Thr Arg Arg
    450             455             460

His Ser Asp Trp Asp Asn Ala Ser Tyr Phe Thr Asn Asp Gly Phe Glu
465             470             475             480

Leu Gly Gly Pro Arg Asp Ala His Gly Thr Leu Asn Arg Glu Gly Leu
```

-continued

```
                485                    490                    495

Ile Gly Tyr Glu Thr Arg Pro Trp Asn Ile Ser Leu Asn Tyr Ile Ile
            500                    505                    510

Lys Val His Tyr
        515
```

SYSTEMS AND METHODS FOR GENERATING BACTERIOPHAGES ADAPTED TO INFECT A TARGET BACTERIAL STRAIN

CROSS-REFERENCE TO RELATED APPLICATIONS

This application is a national phase application under 35 U.S.C.§ 371 of International Application No. PCT/US2020/039527, filed Jun. 25, 2020, which claims the benefit of priority to U.S. Provisional Patent Application Ser. No. 62/867,388, filed Jun. 27, 2019. The entire content of each application is hereby incorporated by reference herein.

SEQUENCE LISTING

This application is being filed electronically via Patent Center and includes an electronically submitted sequence listing in ASCII format. The .txt file contains a sequence listing entitled "046641-7033US1_ST25.txt" created on Aug. 5, 2025 and having a size of 9,327 bytes. The sequence listing contained in this .txt file is part of the specification and is herein incorporated by reference in its entirety.

BACKGROUND OF THE INVENTION

Society is at the precipice of a medical crisis. Bacteria that inhabit our microbiome and environment are evolving resistance to life-saving antibiotics much faster than the rate that new antibiotics are discovered, characterized, tested, and approved. This crisis originates from two synergistic forces. The first is generated by nature, and referred to here as the mutagenic tetrasect. Conceptually, the tetrasect is the intersection of four mechanisms of mutagenesis of bacteria, including de novo errors in copying DNA, and the transformation, conjugation, and transduction of new DNA elements into the cell. These four mechanisms of introducing adaptability into bacteria are the primary driver of resistance to antibiotics. The second obstacle is generated by humanity, namely, the inability of the medicine-making and medicine-approving process to keep pace with the rate at which bacteria overcome new medicines or measures to control them. These measures are further undermined by the cost (~$1 billion) and time (~10 years) of developing new antibiotics, as well as limited chemical space to build new medicines from existing ones.

SUMMARY OF THE INVENTION

One aspect of the invention provides a method of generating bacteriophages adapted to infect a target bacterial strain. The method comprises: providing host bacteria that are susceptible to phage as input to a host chemostat containing phage; providing target bacteria that are related to the host bacteria, but not susceptible to phage as input to a target chemostat containing phage; filtering outflows from the host chemostat and the target chemostat to isolate phage from the populations of the host bacteria, the target bacteria, and macromolecules; combining the outflows; and introducing the combined outflow into each of the host chemostat and the target chemostat.

This aspect of the invention can include a variety of embodiments. The method can further include: providing additional host bacteria as input to the host chemostat; and providing additional target bacteria as input to the target chemostat. The method can further include: providing resistor bacteria that are derived from the host bacteria, but no longer susceptible to phage as input to a resistor chemostat containing phage, wherein outflows from the resistor chemostat are filtered and combined with the other outflows before introduction into the chemostats.

Another aspect of the invention provides a system for generating bacteriophages adapted to infect a target bacterial strain. The system includes: a host chemostat; a target chemostat; one or more filters fluidically coupled to outlets of the host chemostat and the target chemostat, the one or more filters adapted and configured to filter phage from one or more selected from the group consisting of: bacteria and macromolecules; a first fluidic coupling between the outflows of the host chemostat and the target chemostat; and a second fluidic coupling between output of the one or more filters containing phage and inputs of the host chemostat and the target chemostat.

BRIEF DESCRIPTION OF THE DRAWINGS

For a fuller understanding of the nature of the present invention, reference is made to the following detailed description and accompanying figures:

FIG. 1 depicts exemplary designs of individual chemostat cultures, namely, refugee chambers (left) and selection chambers (right) according to embodiments of the invention. Refugee chambers (left) propagate naïve bacteria (never exposed to bacteriophage), which are directed into selection chambers containing bacteriophage (right). Media fill the chambers, while compressed air agitates the cultures and creates positive pressure for contents to leave via air/media exit needle. Bacterial growth is regulated by rate of media entry, as well as purging via overflow waste needle.

3 mined by calculating efficiency of plating (EOP), a measurement of phage titer of target strain over the titer on the host strain. Dark black squares indicate EOP>0.1, dark grey indicate 0.005<EOP<0.099, light grey indicate EOP<0.005, white indicate that no lysis was observed and black stripes indicate that a strain was not tested.

Figure 5:
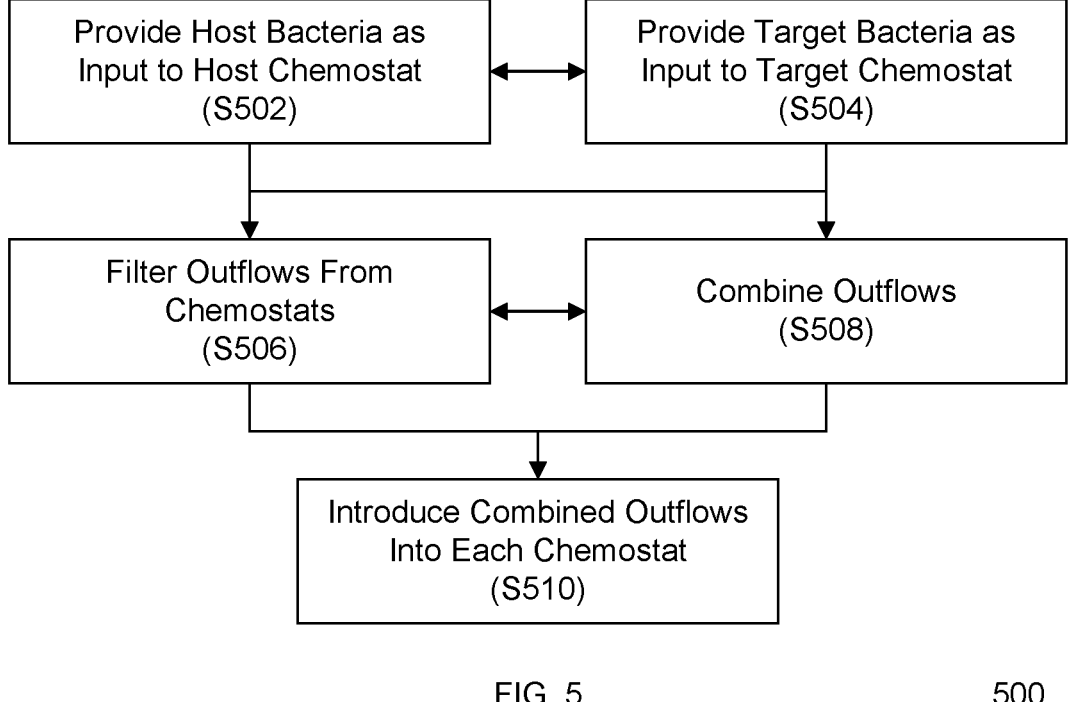

FIG. 5 depicts a method 500 of generating bacteriophages adapted to infect a target bacterial strain according to an embodiment of the invention.

Figure 6:
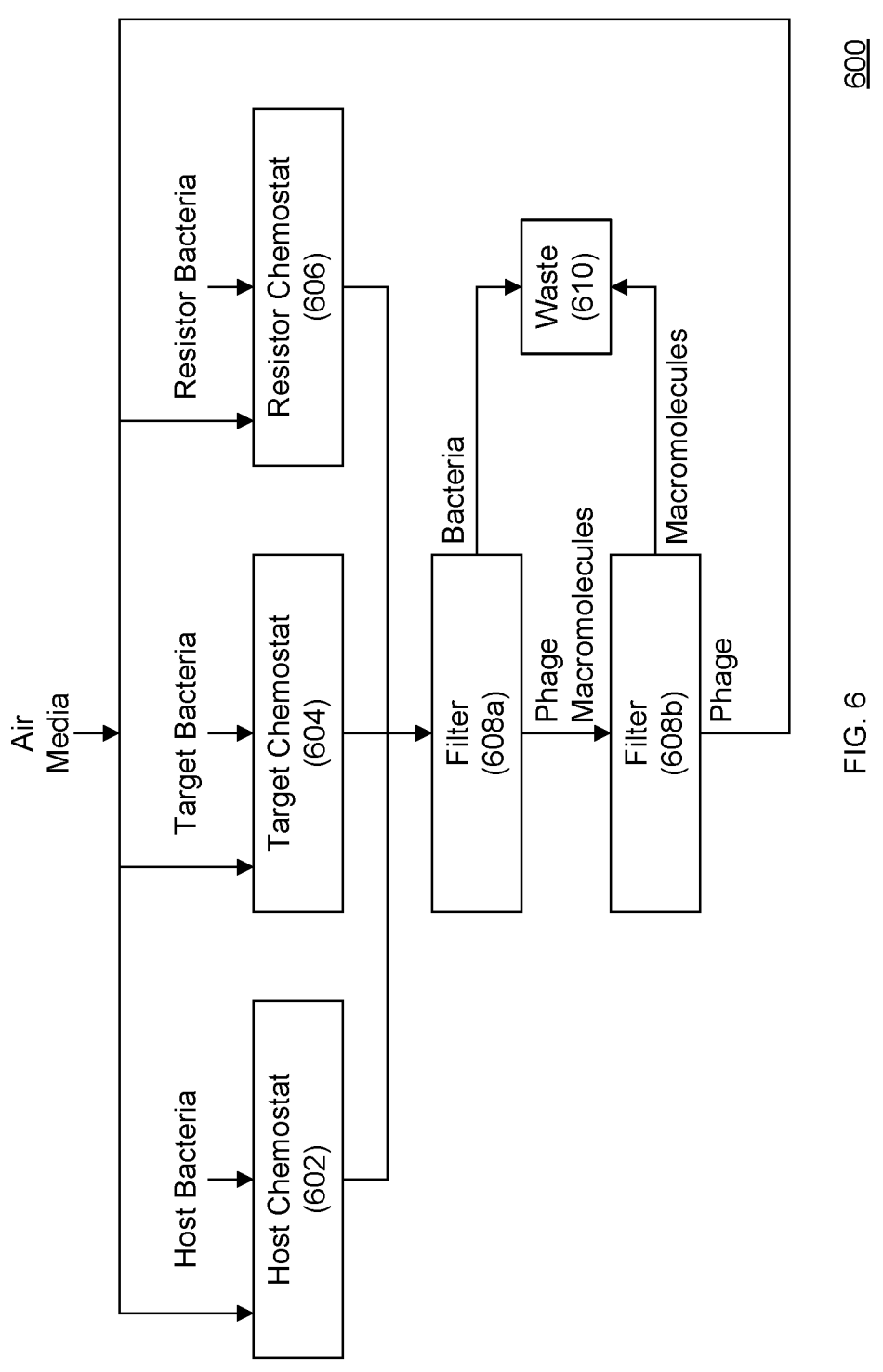

FIG. 6 depicts a system for generating bacteriophages adapted to infect a target bacterial strain according to an embodiment of the invention.

Figure 7:
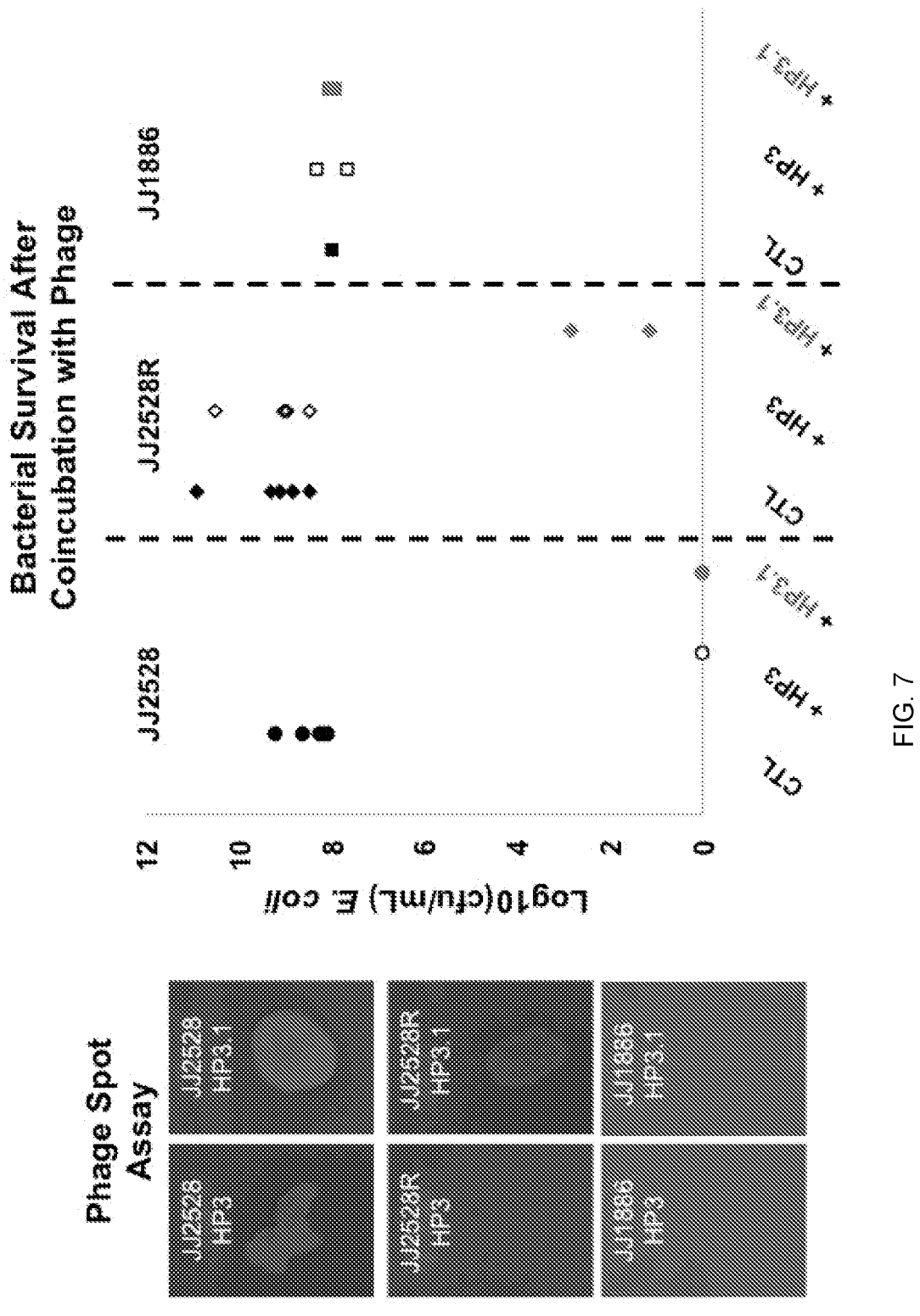

FIG. 7 depicts phage specificity on three *E. coli* strains: host (JJ2528), a target strain (JJ2528R) that acquired resistance to phage HP3, and a non-target strain (JJ1886) that was not able to be infected by phage HP3. As depicted in the left panel, overnight bacterial cultures were suspended in LB top agar and allowed to solidify on an LB plate. 5 μL of phage was spotted on the top agar, and the plates incubated overnight. As depicted in the right panel, overnight bacterial cultures were diluted to an optical density of 0.01 and phage added to an MOI of 1. The mixture was incubated for 4.5 hours in LB, serially diluted and plated, and incubated overnight. Colonies were counted to calculate surviving bacterial titer. Closed, open, and red circles represent untreated, ΦHP3-treated, and ΦHP3.1-treated cultures respectively.

FIG. 8 depicts the use of the evolved phage in the treatment of a murine host infected with *E. coli*. As depicted in the left panel, Swiss Webster, 6 week old, female mice were infected via an intraperitoneal (IP) injection of $10^8$ CFU of phage-resistant strain JJ2528R. One hour following infection, mice were injected IP with $10^9$ PFUs of purified ΦHP3 or evolved ΦHP3.1. Disease severity was assessed at 18 hours post-infection and organs harvested and plated to determine bacterial burden. The middle and right panels depict bacterial burdens for liver and spleen respectively. p-values were generated using a Tukey test. One star (*) indicates p<0.05; two stars () indicates p<0.01, and four stars (**) indicates p<0.0001. Error bars represent the standard deviation and n=10.

Figures 9A, 9B, 9C:
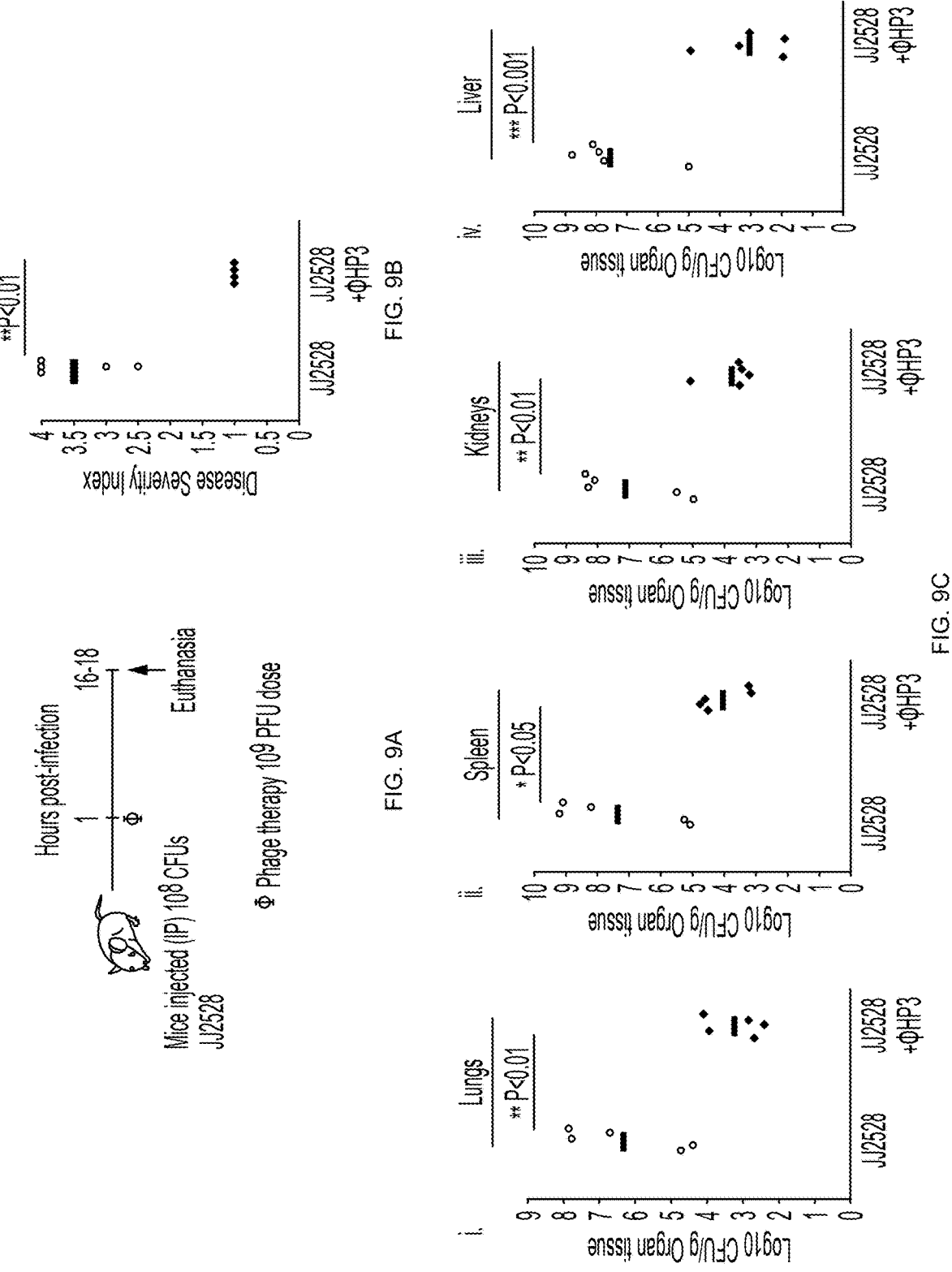

FIG. 9 depicts efficacy after a single dose of phage in a murine model of sepsis according to an embodiment of the invention.

Figure 10:
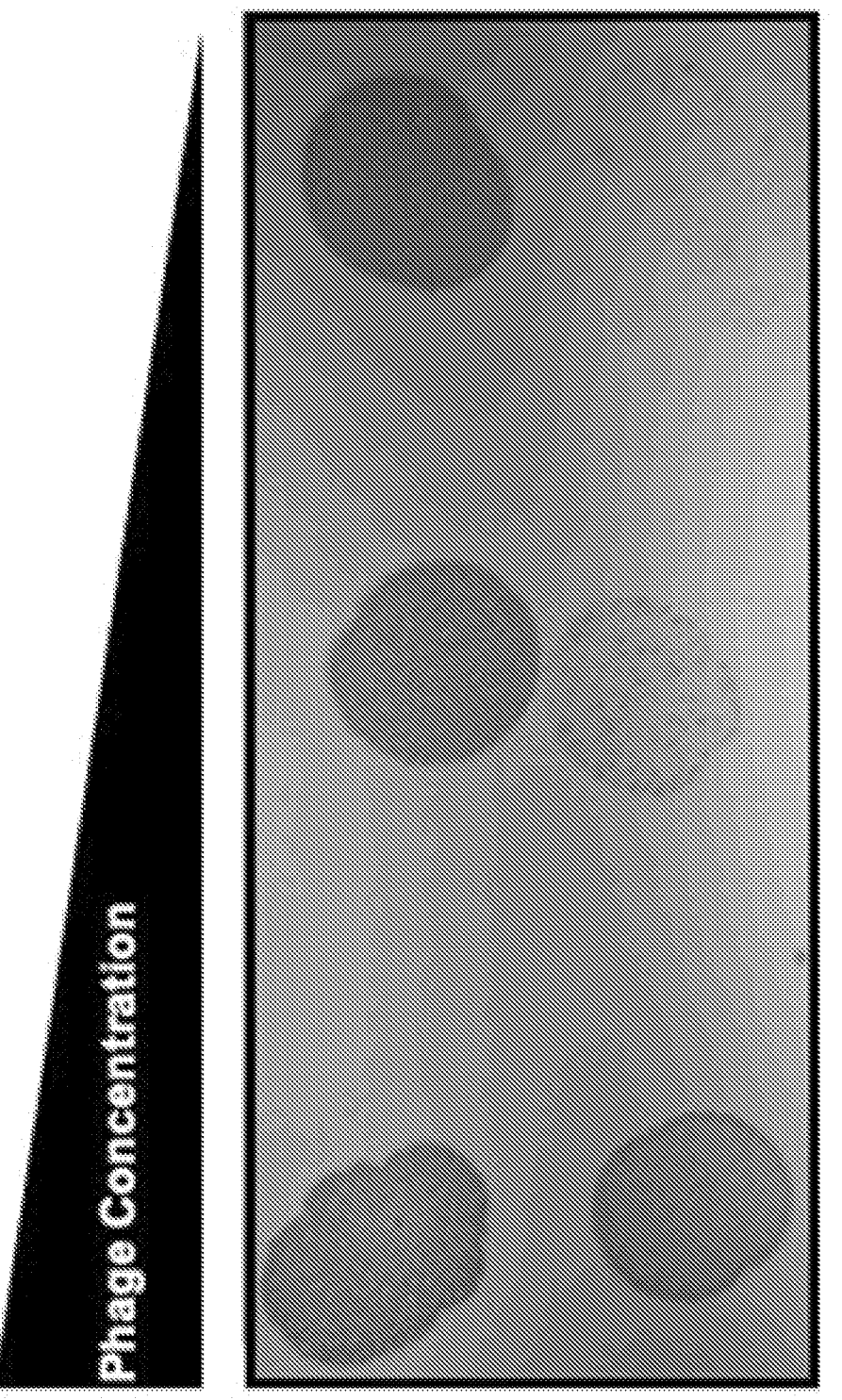

FIG. 10 depicts serial dilutions of purified phage HP3.1 spotted onto a lawn of a clinical ESBL *E. coli* isolate using the double agar overlay method.

FIG. 11. depicts alignment of short tail fiber proteins of HP3 (top line) and HP3.1 (bottom line) based on whole genome sequencing of the two phages.

FIG. 12 depicts predicted structures of short tail fiber proteins (highlighted circle) for phages HP3 and HP3.1 constructed using *E. coli* phage T4 as a guide.

DEFINITIONS

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

As used herein, "host" can refer to a bacterial strain susceptible to phage.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

As used herein, "related" can refer to bacteria that are of the same species, but different strains.

As used herein, "resistor" can refer to any mutant derived from a "target" bacterial strain that is no longer susceptible to phage.

As used herein, "target" can refer to a bacterial strain related (e.g., closely related to a "host" bacterial strain, but not susceptible to phage).

DETAILED DESCRIPTION OF THE INVENTION

Current small molecule antibiotics are limited by the number of chemical substituents possible around a defined, rigid chemical structure. This pales in comparison to the mutagenic power of DNA, with a nearly limitless number of combinations of a four-letter linear code, which confers upon a bacterial cell an equally limitless set of adaptations to overcome antibiotics. However, there is one self-replicating entity with as much, if not more mutagenic potential than bacteria: the bacteriophage.

Phage are viruses that bind, infect, and kill only bacteria, and do so with incredible efficiency. Furthermore, they are the most abundant viruses on Earth, yielding a nearly limitless supply of bactericidal agents that are naturally-derived from our planet's soil and water. Unlike rigid chemical antibiotics, bacteriophage constantly change via mutations in their genetic code, with rare variants arising that are capable of killing pathogenic strains of bacteria.

The invention described herein is a system and associated method for evolving and selecting for rare bacteriophages that infect a target bacterial strain. The system and method are referred to as the Tetrastat.

Embodiments of the invention provide a co-culture system that evolves and eventually selects for rare phage variants that kill clinically-relevant, drug-resistant strains of harmful bacteria. Embodiments of the invention can structure an artificial environment to give phage an evolutionary advantage over bacteria, facilitate iterative growth and death cycles of phage and target host, provide refugee chambers that continuously deliver naïve (never exposed to phage) bacteria into selection chambers, and enable addition of enhanced modules, including chemical and genetic acceleration of mutation, the ability to culture diverse clinical strains of bacteria in common media, and perform these selections in environments that will enhance the efficacy of the phage in patients, including environments such as blood, serum, urine, intestinal contents, and the like.

A Tetrastat, broadly defined, is a modified chemostat array culture system designed to: (1) maintain refugee chambers for growth of the host and target bacteria, (2) direct host and target strains from their individual refugee chambers into respective selection chambers in the presence of phage, (3) permit phage generation and phage-mediated lysis of bacteria in selection chambers, (4) isolate phage derived from all of the selection chambers and combine into a phage pool, (5) disperse the phage pool back into the selection chambers, and (6) remove spent media and bacteria via directed flow, such that features (1)-(5) can cycle indefinitely.

Exemplary Ministats

Referring now FIG. 1, one embodiment of a ministat includes four needles of varied length (short, S; medium, M; long, L) to direct air and media flow.

The refugee chambers can be connected such that media enters S, air enters L, and air/media exit M.

The selection chambers are connected such that the phage pool in media or other environmental conditions enter S, air/media from their respective refugee chambers enter L, and air/media exit M.

All chambers can include a second long needle that can purge media and direct it to an overflow waste container when necessary.

Exemplary Tetrastat Schematic

Figure 2:
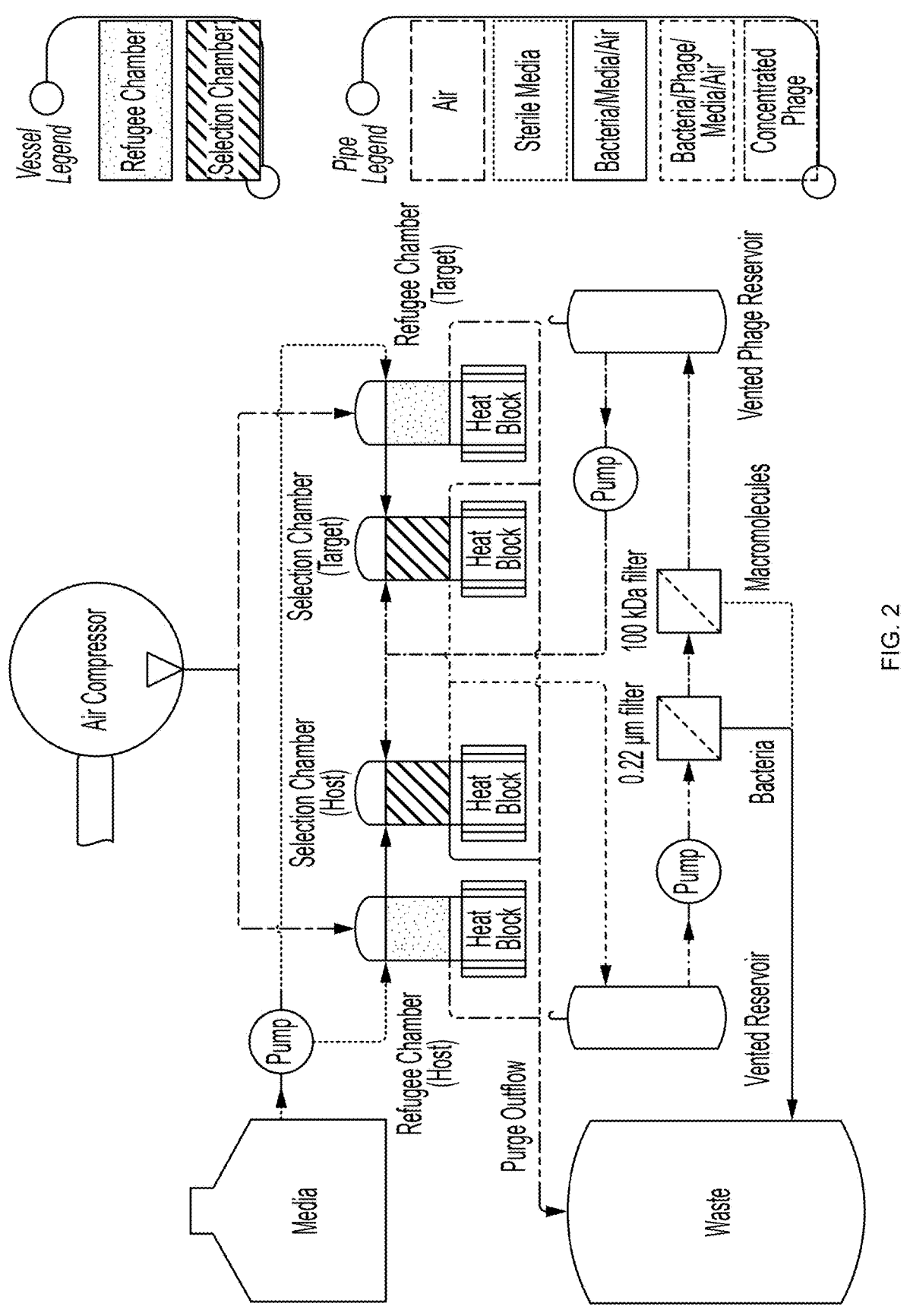
FIG. 2 is an engineering schematic of the Tetrastat system according to embodiments of the invention. When assembled, the Tetrastat system provides features (1)-(6) stated under "Detailed Description of the Invention". Chemostat chambers can be built as depicted in FIG. 1. Media and air can be directed into refugee chambers by a peristaltic pump and air compressor respectively (green and blue lines). Positive pressure forces air and media containing bacterial cells into selection chambers with phage, and subsequently to a vented reservoir (black and yellow lines). Bacteria and spent media can be removed to waste either through tangential flow filtration (e.g., 0.22 μM filter) or purging from chemostat cultures (black lines). Phage-containing retentate from the 100 kDa filter can be directed back into selection chambers via peristaltic pump (red lines).
Figure 3:
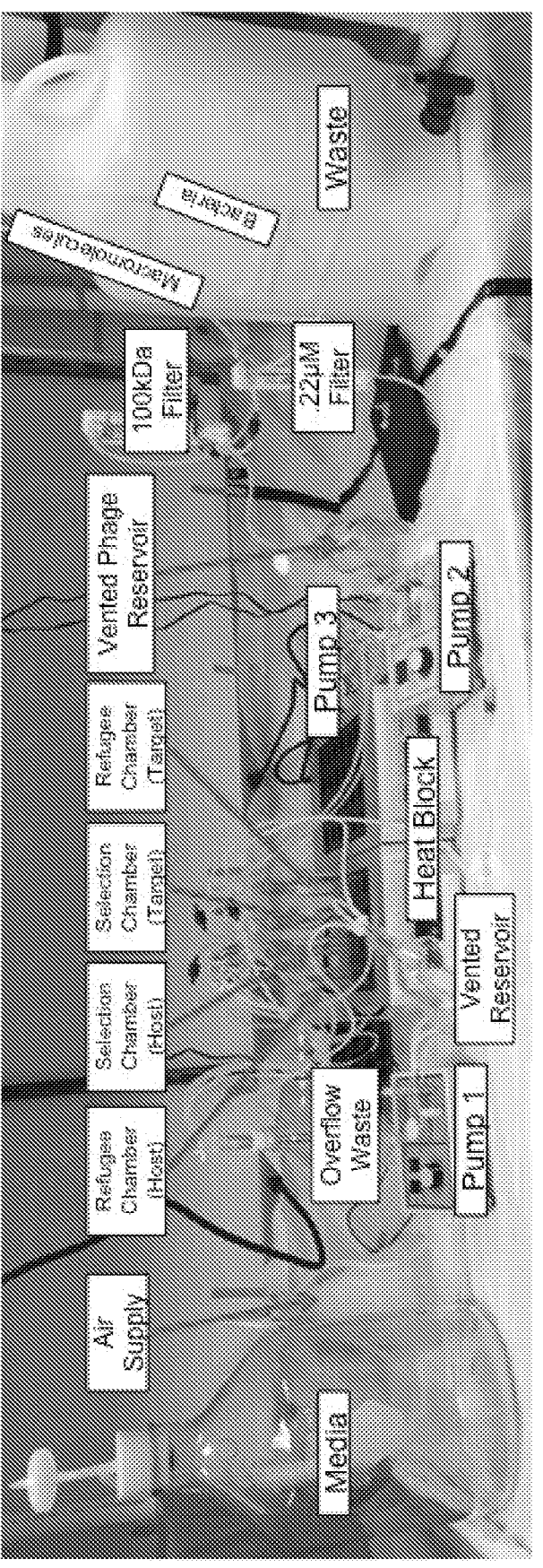
FIG. 3 depicts an assembled Tetrastat system according to an embodiment of the invention. Chemostat array cultures and components can be connected as described above in the context of FIGS. 1 and 2. This current setup is capable of continuously maintaining host and target bacterial strains for 1 week with 10 L of LB media. (Continuous coculture times can vary depending on the bacterial strains and culture conditions and can generally be increased through the use of additional media.)

Exemplary schematics for the Tetrastat system are presented in FIGS. 2 and 3. Compressed air and introduction of media via peristaltic pumps combine to create positive pressure that forces ministat contents from refugee chambers to selection chambers, and from selection chambers to a vented carboy, which releases pressure. Check valves are placed between the air lines and refugee chambers, and between the refugee chambers and selection chambers to ensure proper directional flow and mitigate issues arising from pressure differences in the ministats. Fine-tuning the rate of media entry permits maintenance of cell number in cultures by avoiding overgrowth or clearance.

The spent media from the selection chambers is forced through tangential flow filters arranged in tandem via peristaltic pump. In one embodiment, filter #1 contains 0.22 µM pores, which permit entry of phage, but not bacteria. Thus, concentrated bacteria exit the retentate, while phage exit the permeate. The permeate (phage-containing fraction) from filter #1 is connected to filter #2, which, in one embodiment, contains 100 kDa pores. This filter permits entry of media and most macromolecules, but not phage. Thus, concentrated phage can exit the retentate, while media and bacterial products exit the permeate. The retentate from filter #1 and permeate from filter #2 can be directed to waste.

Figure 4:
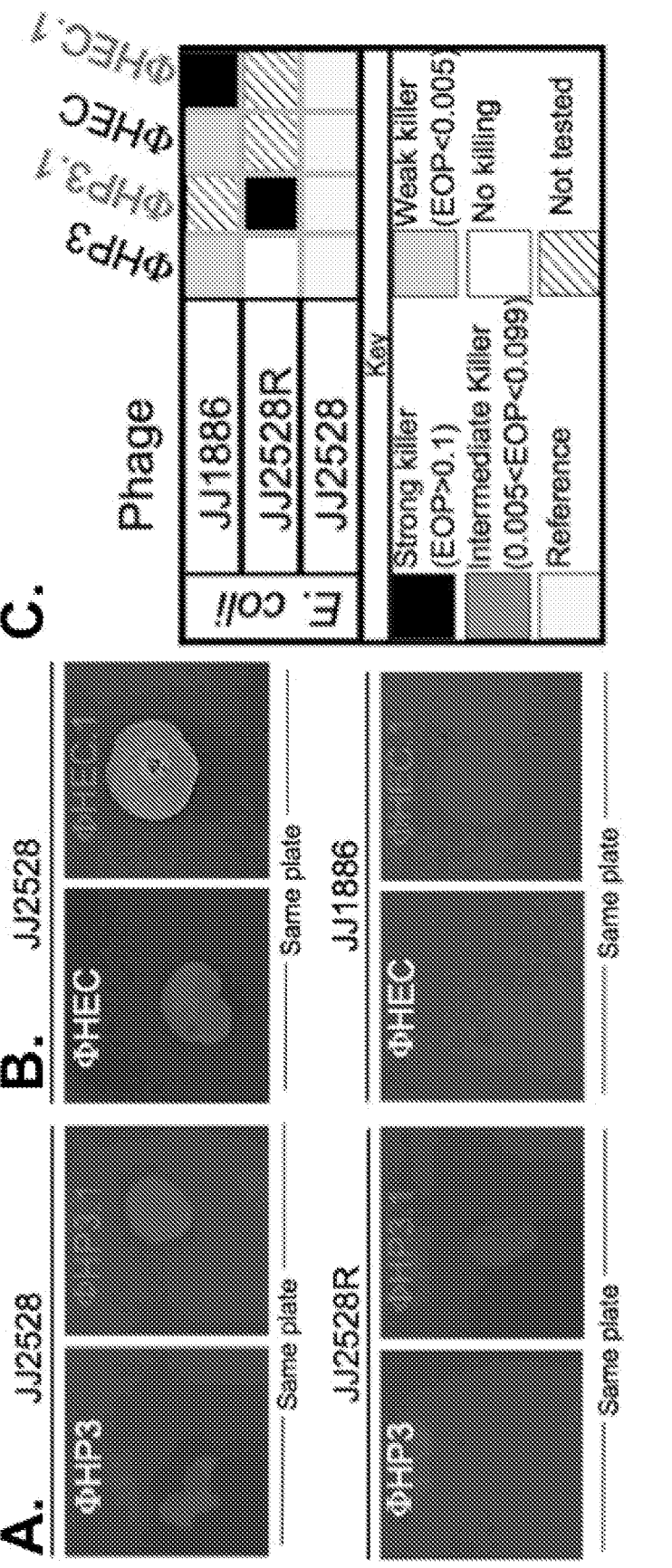
FIG. 4 depicts lytic activity of evolved phages after continuous evolution and passaging between host and target bacteria. Panel (A) depicts plaque formation of ΦHP3 and evolved ΦHP3 (labeled ΦHP3.1) plated on pathogenic E. coli strain JJ2528 (host strain) and a resistant derivative of the host strain, JJ2528R. Panel (B) depicts plaque formation of ΦHEC (cocktail of 4 phages—ΦHP3, ΦEC1, ΦCF2, and ΦCF2s) and evolved ΦHEC (labeled ΦHEC.1) plated on E. coli strain JJ2528 (host) and partially resistant pathogenic E. coli strain, JJ1886. As depicted in Panel (C), the killing potential of each phage was deter-

The retentate from filter #2 (concentrated phage pool) can be directed to another vented carboy. The phage can be forced back into the selection chambers via peristaltic pump. This phage pool will contain novel variants that have arisen through this iterative process (FIG. 4).

Exemplary Method

Referring now to FIG. 5, one embodiment of the invention provides a method 500 of generating bacteriophages adapted to infect a target bacterial strain.

In step S502, host bacteria that are susceptible to phage can be provided as input to a host selection chemostat containing phage.

In step S504, target bacteria that are related to the host bacteria, but not susceptible to phage can be provided as input to a target selection chemostat containing phage.

In step S506, outflows from the host selection chemostat and the target selection chemostat can be filtered to isolate phage from the populations of the host bacteria, the target bacteria, and macromolecules.

In step S508, the outflow can be combined.

In step S510, the combined outflow can be re-circulated into the host selection chemostat and the target selection chemostat.

Exemplary System

Referring now to FIG. 6, another embodiment of the invention provides a system 600 for generating bacteriophages adapted to infect a target bacterial strain. The system 600 can include a host chemostat 602, a target chemostat 604, and a resistor chemostat 606. Each chemostat 602, 604, 606 can receive one or more inputs such as air, media, phage, and bacterial strains. The bacterial strains can be maintained in a respective refugee chamber as described and depicted in the context of FIG. 2.

The outflows of the chemostats 602, 604, 606 can be coupled to one or more filters 608a, 608b. Filters 608a, 608b can receive the combined outflows as depicted or can be in parallel followed by combination after filtration. A variety of filter types and sizes can be utilized. In one embodiment, the first filter 608a is sized to remove bacteria and the second filter 608b is sized to concentrate the phage. Filters sizes can be selected to control the composition of toxins, virulence factors, and other macromolecules that are re-circulated into the selection chambers 602, 604, 606.

Components of system 600 can be controlled (e.g., through hardware and/or software) to maintain specified parameters (e.g., temperature, pressure, flow rate, and the like). Components can be set to different modes, such as incubation and cleaning. For example, in a cleaning mode, chemostats 602, 604 can be controlled to create a bactericidal temperature (e.g., 95° C.).

The system 600 can include directional-flow devices such as one-way or check valves. The system can include one or more pumps such as peristaltic pumps to facilitate fluid flow. Such pumps can be communicatively coupled to a controller. The system can include one or more sensors such as temperature, pressure, and optical sensors in communication with a controller programmed to use inputs from the sensors as feedback to maintain specified conditions. Exemplary optical sensors adapted and configured for placement over optically transparent tubing are described in U.S. Patent Application Publication No. 2018/0360365.

Further Embodiments

Optical density and media flow-rate can be regulated electronically to precisely control the bacterial growth, filter pressure, and phage pool dispersal. This can be achieved by including spectrophotometers, valves, pressure gauges, and dedicated pumps integrated by software. Such features permit experimental tailoring of the structured environment and optimized phage production.

De novo bacterial resistors can be directed from the target population into additional refugee and selection chambers. This design promotes selection of phages that lyse the target strain and resistor mutants. In principle, the resulting phage cocktail will reduce spontaneous bacterial resistance to a phage therapy regimen.

Some embodiments can include separate filter systems for host and target/resistor strains. The current design utilizes one central filter system to isolate and concentrate phage. It may be beneficial to place one filter system between the host selection chamber and the target/resistor selection chambers, and vice versa. This dual filter system could increase the selective pressure for stable phage that can lyse target/resistor strains.

Feeder modules can provides enhanced features, including adding polymerase chain reaction (PCR) products generated from error-prone PCR to the phage pool. This permits greater mutagenesis when a large "evolutionary leap" is required, such as for phages moving between distantly related bacteria. This feature may also be achieved by developing novel mutagenic host strains with error-prone DNA polymerases or by exposing the phage pool to a mutagen such as UV light or mutagenic chemicals.

"Phenotype filter" modules can induce favorable phenotypes and/or therapeutically useful phage. For example, evolved phage may be directed to cultures that contain target bacteria grown in an adapted version of human blood or other fluids (urine, fecal or intestinal contents, conditions that simulate the human host such as organotypic cultures, cerebral spinal fluid, and the like). Phages active in these environments thus contain both the specificity and activity in environments meant to mimic the human patient.

Industrial engineering, bioengineering and microfluidic principles can be employed to scale-up or -down the described design and possible iterations. Scaling-up provides a means for serving medical, agricultural, and environmental demand. Scaling-down allows high-throughput experimental designs. For example, embodiments of the invention can be fabricated on a single micro-fluidic chip using a variety of techniques including casting, molding, machining, thermomolding, thermosetting, injection molding, vacuum forming, additive manufacturing (also known as 3D printing), and the like.

Embodiments of the invention can be utilized to investigate viral evolution and evolutionary dynamics in general.

Embodiments of the invention have the ability to evolve fungal and mammalian viruses. Similar designs can be modified to investigate any form of microbial evolution.

Working Example

Working Example 1—Efficacious Anti-Bacterial in Two Weeks

The potential for even environmentally-derived phage to be efficacious at controlling bacterial infections with little cost and quick turnaround is illustrated by the data presented in FIG. 9. In just 14 days, a novel phage was discovered, purified, characterized, and tested against a representative of the currently circulating pandemic strain of multi-drug resistant E. coli in a murine model of bacteremia. Just a single dose of the phage reduced the bacterial burden 3-6 logs in all major organs and prevented death of the E. coli-infected murine host. Panel A shows the order of the experiment. Panel B shows animal health with and without phage. Panel C shows the bacterial burden in organs with and without phage. Panel D shows the phage replication at the site of infection. Panel E shows the structure of the phage used in this study.

Working Example 2—Evolved Phage HP3.1 is Broadly Active Against all Other Resistor E. coli Strains Phage HP3.1 that was evolved in the Tetrastat system against the original resistor E. coli (resistant to phage HP3) exhibited killing activity against every resistant E. coli that emerged from this process. This is shown in Table 1 below.

TABLE 1

| E. coli Strain | HP3 Titer | HP3.1 Titer |
|---|---|---|
| JJ2050 | 6.73E10 | 4.74E9 |
| JJ2050-1 | | 4.16E8 |
| JJ2050-2 | | 3.34E8 |
| JJ2050-3 | | 9.29E8 |
| JJ2528 | 8.32E10 | 4.47E10 |
| JJ2528-1 | | 3.56E9 |
| JJ2528-2 | | 3.78E9 |
| JJ2528-3 | | 4.45E9 |
| JJ2528-4 | | 5.42E9 |
| JJ2528-5 | | 1.39E9 |
| JJ2528-6 | | 6.61E8 |
| JJ2528-7 | | 6.53E8 |
| JJ2528-8 | | 1.9E9 |
| JJ2528-9 | | 1.93E9 |
| JJ2528-10 | | 1.48E9 |
| JJ2528-11 | | 1.25E9 |
| JJ2528-12 | | 2.47E9 |
| JJ2547 | 3.16E11 | 3.01E10 |
| JJ2547-1 | | 6.32E9 |
| JJ2547-2 | | 4.27E10 |
| JJ2547-3 | | 9.51E10 |
| JJ2547-4 | | 1.07E10 |
| JJ2547-5 | | 8.13E9 |
| JJ2547-6 | | 2.57E9 |

The cells containing numbers (representing a spot assay titer (PFU/mL)) indicate killing. The empty cells indicate no killing. Phage HP3 is capable of killing strains JJ2050, JJ2528, and JJ2547. However, all resistor strains (labeled under the parent strains), are not killed by phage HP3. Relative to HP3, Tetrastat-evolved phage HP3.1 is very effective at killing all the resister strains that arose against phage HP3, as well as being able to kill the original parent strain. This implies that the Tetrastat system generated a mutant phage that expanded its host range, resulting in lysis of resistant E. coli strains.

Working Example 3—Evolved Phage HP3.1 Kills Clinical Isolate of ESBL E. coli Applicant tested if the phage evolved in the Tetrastat system was capable of killing a strain of E. coli from a clinical case.

Referring to FIG. 10, serial dilutions of purified phage HP3.1 were spotted onto a lawn of a clinical ESBL E. coli isolate using the double agar overlay method. High concentrations of phage clear the lawn (top row), while diminishing concentrations (left to right) reveal small individual plaques. This assay indicates that HP3.1 is virulent (capable of killing bacteria with a low dose) against this E. coli.

Tetrastat-evolved phage HP3.1 was next combined with 3 other phages for human phage therapy of a urinary tract/bladder infection on a compassionate use basis. Consistent with the data presented here, the original ESBL E. coli could not be detected in the patient-derived serum and urine samples. This suggests that a phage cocktail containing phage HP3.1 was effective at killing bacteria in a clinical application of human phage therapy.

Working Example 4—Evolved Phage HP3.1
Possesses a Mutated Short Tail Fiber

Bacteriophage tail fibers typically recognize and bind to specific bacterial receptors at the cell surface to permit infection. Conversely, bacteria will mutate their surface receptors to avoid infection by phages. Thus, tail fibers represent an important target for evolutionary adaptation.

Referring to FIG. 11, the short tail fiber proteins of HP3 (top line) and HP3.1 (bottom line) were aligned based on whole genome sequencing of the two phages. This revealed two adjacent amino acids (highlighted) that changed from a positively charged and polar residue (HP3, lysine and tyrosine respectively) to two positively charged residues (HP3.1, arginine and histidine).

Referring to FIG. 12, predicted structures of short tail fiber proteins (highlighted circle) for phages HP3 and HP3.1 were constructed using E. coli phage T4 as a guide. Interestingly, this analysis placed the mutated residues at the tip of the tail fibers (bottom of structure). This suggests a mechanism whereby a mutated short tail fiber in evolved phage HP3.1 changes its affinity and/or specificity for the bacterial cell surface receptor, permitting broader recognition and infection.

Collectively, these data argue for the ability of the Tetrastat system to generate evolved phages de novo that possess unique adaptations to target and kill a broad range of previously-resistant bacterial isolates. Furthermore, clinical application of evolved phage HP3.1 supports employment of the Tetrastat system to safely develop novel phage cocktails for human phage therapy.

EQUIVALENTS

Although preferred embodiments of the invention have been described using specific terms, such descriptions are for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A method of generating bacteriophages adapted to infect a target bacterial strain, the method comprising:

exposing host bacteria that are susceptible to an input phage to the input phase in a host chemostat;

exposing target bacteria that are the same species as the host bacteria, but a different strain which acquired resistance to and are not susceptible to the input phage as input to a target chemostat containing the input phage;

filtering outflows from the host chemostat and the target chemostat to isolate phage from the host chemostat and the target chemostat;

combining the outflows into a phage pool;

introducing the phage pool back into each of the host chemostat and the target chemostat; and repeating the steps of exposing the host bacteria and target bacteria to the input phage, filtering the outflows, combining the outflows into a phage pool, and introducing the phage pool back into each of the host chemostat and the target chemostat at least until a bacteriophage adapted to infect the target bacteria is generated.

2. The method of claim 1, further comprising, while repeating the steps of exposing the host bacteria and target bacteria to the input phage, filtering the outflows, combining the outflows into a phage pool, and introducing the phage pool back into each of the host chemostat and the target chemostat:

providing additional host bacteria as input to the host chemostat; and providing additional target bacteria as input to the target chemostat.

3. The method of claim 1, further comprising:

exposing resistor bacteria that are the same species, but different strain from the host bacteria, which are not the target bacteria and also have acquired resistance to and are no longer susceptible to the input phage as input to a resistor chemostat containing the input phage, wherein outflows from the resistor chemostat are filtered and combined with the other outflows into the phage pool before introduction into the chemostats, and then repeating the steps of exposing the host bacteria, target bacteria, and resistor bacteria to the input phage, filtering the outflows, combining the outflows into a phage pool, and introducing the phage pool back into each of the host, target, and resistor chemostats at least until a bacteriophage adapted to infect the target bacteria and the resistor bacteria is generated.

4. A system for generating bacteriophages adapted to infect a target bacterial strain, the system comprising:

a host chemostat;

a target chemostat;

one or more filters fluidically coupled to outlets of the host chemostat and the target chemostat, the one or more filters adapted and configured to filter phage from one or more selected from the group consisting of: bacteria and macromolecules;

a first fluidic coupling between the outflows of the host chemostat and the target chemostat; and a second fluidic coupling between output of the one or more filters containing phage and inputs of the host chemostat and the target chemostat.

* * * * *